United States Patent [19]

Vaughan et al.

[11] Patent Number: 5,663,420
[45] Date of Patent: Sep. 2, 1997

[54] DEPOLYMERISATION

[76] Inventors: Patrick William Vaughan, Bedw Arian, Glyn Garth, Menai Bridge, Anglesey, United Kingdom, LL595NP; Donald James Highgate, The Wilderness, Holmbury Hill Road, Holmbury St. Mary, Dorking, Surrey, United Kingdom, RH5 6NS

[21] Appl. No.: 353,965

[22] Filed: Dec. 12, 1994

Related U.S. Application Data

[63] Continuation of Ser. No. 162,481, Dec. 3, 1993, abandoned.

[30] Foreign Application Priority Data

Dec. 4, 1992 [GB] United Kingdom ............ 9225461

[51] Int. Cl.$^6$ .................................................. C07C 67/00
[52] U.S. Cl. .......................................................... 560/216
[58] Field of Search .................................................. 560/216

[56] References Cited

U.S. PATENT DOCUMENTS

| | | | |
|---|---|---|---|
| 2,030,901 | 2/1936 | Strain | 560/216 |
| 2,341,282 | 2/1944 | Mark | 560/216 |
| 2,858,255 | 10/1958 | Segui et al. | 560/216 |
| 3,494,958 | 2/1970 | Mannsfeld et al. | 560/216 |
| 3,868,410 | 2/1975 | Hordenico et al. | 560/216 |
| 3,886,202 | 5/1975 | Tatsumi et al. | 560/216 |
| 3,974,206 | 8/1976 | Tatsumi et al. | 560/216 |
| 4,360,461 | 11/1982 | Fuchs et al. | 260/239.3 |

FOREIGN PATENT DOCUMENTS

| | | |
|---|---|---|
| 0046183 | 2/1982 | European Pat. Off. . |
| 460009 | 1/1937 | United Kingdom . |

OTHER PUBLICATIONS

*Method of depolymerising thermoplastics*, Anon., vol. 87 Chemical Abstracts No. 2,11 Jul. 1977, p. 2; col. 2, astract No. 6399e.

*Method of depolymerising thermoplastics*, Disclosed Anonymously, 157 Research Disclosure May 1977, p. 18 No. 15743.

*Monomer recovery by pyrolysis of poly(methyl methacrylate)*, Kaminsky, W. and Franck, J., Journal of Analytical and Applied Pyrolysis, 19 (1991) 311–318.

*Primary Examiner*—Paul J. Killos
*Attorney, Agent, or Firm*—Bernstein & Associates

[57] ABSTRACT

A polymer such as poly(methyl methacrylate) is depolymerized, e.g., to give MMA, by heating the polymer in a fluidized bed at a temperature below the autoignition point of the monomer.

9 Claims, 1 Drawing Sheet

DEPOLYMERISATION

This is a continuation of application Ser. No. 08/162,481, filed Dec. 3, 1993 now abandoned.

FIELD OF THE INVENTION

This invention relates to a depolymerisation process.

BACKGROUND OF THE INVENTION

Monomer can often be recovered from polymer waste by depolymerisation. In particular, PMMA, i.e. poly(methyl methacrylate), gives methyl methacrylate at elevated temperature. For many years, PMMA has been successfully depolymerised by contact with molten lead at about 500° C.; the monomer MMA can be obtained in a purity of more than 98% (here and throughout, percentages are given by weight unless otherwise specified).

Although this process gives MMA of high purity, the use of lead is undesirable, from an environmental viewpoint. Further, small amounts of lead as a contaminant are extremely difficult to remove from the monomer, reducing the range of commercial products for which the recovered monomer is acceptable. Higher purity would be desirable, and in particular substantial freedom from byproducts such as methyl isobutyrate which is nonpolymerisable, smelly and difficult to separate from MMA.

Kaminsky et al, J. Anal. App. Pyrolysis 19 (1991) 311–318, disclose the recovery of MMA by pyrolysing PMMA in an indirectly-heated fluidised-bed process. At 450° C., more than 97% of the PMMA was recovered as monomer.

SUMMARY OF THE INVENTION

It has now been found, according to the present invention, that effective depolymerisation of PMMA and other polymers can be achieved in a fluidised-bed process at a relatively low temperature. In particular, the temperature is below the autoignition point of the monomer (c. 425° C. for MMA), thereby making the process not only potentially more economical but also much safer than the process described by Kaminsky et al. Despite the lower temperature, e.g. from 300° C. or 350° C. up to 400° C. or 420° C., the reaction rate remains high, the purity is significantly higher, and the process is thus of commercial importance.

On the simplest level, the novel process overcomes an apparent prejudice against operating the depolymerisation of PMMA at temperatures much below 500° C. The results that are thus achieved are surprising, since very high grade monomer is obtained under intrinsically safe conditions, in a bed which is apparently self-regulating and limited by heat-transfer coefficient (HTC) rather than absolute temperature. Further, the content of volatiles in the monomer vapour is surprisingly low. This combination of effects could not be expected, on the basis of the given prior art.

In a conventional gas-fluidised bed it is difficult to achieve heat transfer coefficients which exceed 500–600 W/m².K. On this basis it would be expected that many of the larger polymer particles would heat until they soften and therefore foam prior to depolymerisation into MMA vapour. In this condition, they would float to the top of the bed where the HTC would decrease still further and the bed would choke unless the working temperature was very much increased. In the present invention, the polymer particles have been shown to ablate and depolymerise from the surface without foaming. This process allows the particles to remain within the body of the bed where the necessary high HTC can be maintained, contributing to high output levels.

Although this invention will be described by way of illustration with respect to the production of MMA by the depolymerisation of PMMA, other depolymerisation processes may be so operated. The process is particularly applicable to the production of those monomers including a $CH_2=CR-$ group, i.e. in which a polymer of the acrylate type has no α-H atom. Specific polymers that may be depolymerised are polyethylene terephthalate (that has been pre-treated with alcohol), isoprene and styrene.

BRIEF DESCRIPTION OF THE DRAWINGS

The invention is illustrated in the drawings in which like reference characters designate the same or similar parts throughout the figures of which.

DESCRIPTION OF THE INVENTION

Figure 1:
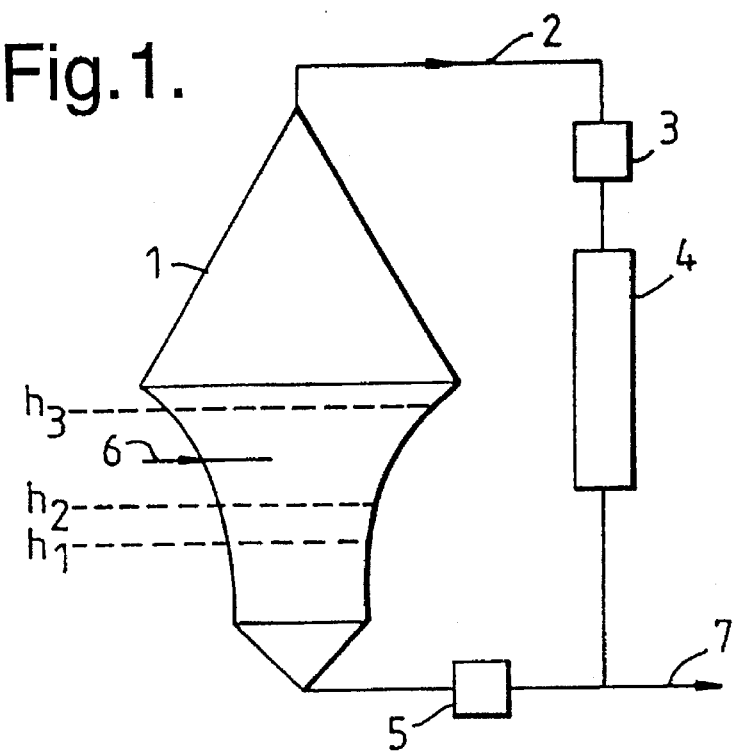
FIG. 1 is a schematic illustration of a preferred embodiment of the present invention.

The Figures illustrate, schematically, embodiments of apparatus suitable for use in a process according to the invention. The essential components of a recycling system are a fluidised bed chamber (1) and a recycling line (2) for gas via a condenser (4) and a cyclone (3) where entrained solids are removed, the circulation being driven by a fan (5). An inlet (6) for polymer and an outlet (7) for monomer are provided. The bed height is h1 when static, h2 when fluidised by inert gas, and h3 when fluidisation is additionally driven by vapour of reaction, as described in more detail below.

The fluidised bed may be of known type. It preferably comprises particles of an inert material such as SiC, silica or alumina. Alumina is preferred with respect to, say, silica; notwithstanding its greater density which requires increased gas circulation pressures, there does not appear to be any adverse effect on the heat transfer or throughput rates once vapour-driven fluidisation has become established. The particles are, for example, 10–1000 µm, e.g. 50–300 µm, in diameter.

The bed may be heated by any suitable means, directly or indirectly. For example, heating elements may be provided in the reaction chamber. Alternatively or in addition, quartz-iodine lamps may be used, or mercury-emitting discharge lamps that may emit in the visible spectrum and in the UV at wavelengths of 200 to 300 nm, to enhance depolymerisation. Indirect heating may be particularly suitable for low temperature depolymerisation.

An inert gas such as nitrogen may be used to initiate fluidisation of the bed in which the polymer is depolymerised. A characteristic of the depolymerisation of PMMA at least is that, following fluidisation of the bed by inert gas (which provides for the very high heat transfer coefficients needed by heating elements, and to initiate the depolymerisation of the PMMA first added to the bed), fluidisation is soon augmented by vapour evolved from the depolymerisation process. In the depolymerisation phase, when the bed is effectively driven by the evolved vapour, it has been found that the bed is essentially self-stabilising and therefore quite controllable. The inert gas flow helps to control the residence time of the vapour at high temperature, e.g. at a superficial velocity of 1 to 10 cm/sec for a given bed particle diameter.

Accordingly, the novel process involves gas circulation with a superimposed vapour flow, comprising generation in the bed and vapour removal as condensate in the condenser. During vapour-driven fluidisation, there exists the possibility of controlling the fluidisation and depolymerisation process by control of vapour pressure. Both the quality of fluidisation and the activity of the depolymerisation process are largely dependent upon the vapour cycle during vapour-driven fluidisation, and it has been found that if a low temperature vapour "trap" is included as the last stage of the condenser system, then very small changes in the temperature of this stage, e.g. by about 1.5° C., from –4 to –2.5° C., have a profound effect upon the throughput as measured by the rate of condensation in the primary condenser sections. For example, as the temperature of a cold vapour control stage increases from –4 to –2.5° C., the rate of depolymerisation falls sharply; as the temperature decreases, the rate of depolymerisation rises rapidly and immediately.

Since the volume of the bed is expanded enormously when depolymerisation is occurring, some means may be required in order to remove particles of the bed entrained with the flow of monomer vapour. For example, a cyclone may be provided; the separated particles can then be returned directly to the reaction chamber. A suitable cyclone may be provided with an impeller. The exit temperature of the inert gas stream plus monomer vapour may be less than 250° C., so that a simple pressed metal or cast aluminum impeller may be used.

In one embodiment of apparatus for use in the present invention, the reaction chamber is modified so that it has a variable area throat, in order to make it fully self-regulating in the region where evolved vapour from the depolymerisation process is driving the fluidisation. A suitable design of chamber is generally cylindrical, its diameter increasing towards the top, e.g. trumpet-shaped. Additional control functions are variation of the inert gas flow, the rate of polymer input, and possibly also temperature conditions in the condenser.

In another embodiment of apparatus for use in the invention, the bed particles passing to the top of the reaction chamber are recirculated. In a circulating bed, a significant proportion of the bed material is kept constantly in transit out of the bed through a cyclone and back into the bed via a valve. This embodiment allows the polymer input to be combined with the return flow of bed material.

These two alternative embodiments will now be described by way of example only with reference to the accompanying, schematic drawings. The embodiments are respectively shown in FIGS. 1 and 2.

In the apparatus shown in FIG. 1, the cross-section of the bed container 1 is designed to match the increasing vapour flow from the process. This is an active part of the bed-fluidising region, not a transport disengagement device. The principle is to provide a parallel cross-section for the gas fluidised bed operation, and an exponentially increasing cross-section for the depolymerisation phase to operate in.

Figure 2:
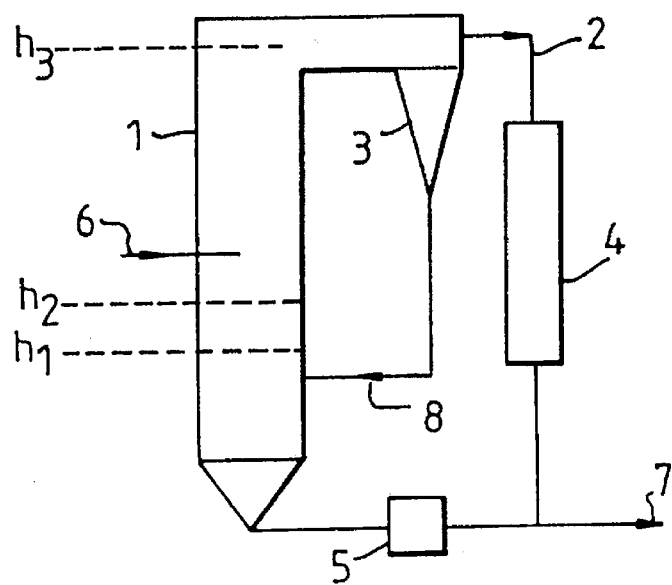
FIG. 2 is a schematic illustration of an alternative embodiment of the present invention.

The apparatus of FIG. 2 provides for particle circulation and for a circulating bed in which a controlled part of the bed material leaves the reactor and is recirculated through a hydrodynamic valve 8. This may be incorporated into a bed material treatment process for the removal of waste products.

Accordingly, whether or not all such apparatus features as are shown in the drawings are adopted, a satisfactory rate of depolymerisation can be controllably maintained while polymer is introduced up to 40, e.g. 2030, kg/h per 0.1 m² of active bed. The polymer is suitably introduced into the reaction chamber, e.g. a stainless steel vessel, by means of a screw feed. This feed is preferably above the normal height of the bed, in order to prevent the screw being heated by contact with the bed, thus preheating the polymer and causing the heated polymer to adhere to the screw. This and other potential problems are also minimised by the addition of a nitrogen entrainment flushing system to prevent back-flow of vapour along the screw. Using apparatus of this type, in a reaction chamber having internal base dimensions of 40 cm×40 cm and a PMMA scrap feed of 30 kg/h, it has been demonstrated that the bed is stable both in the initial phase and in the presence of depolymerisation. The heaters have been operated at full load for many hours, with an operating temperature only 5°–50° C. above a mean bed temperature of 385° C. The bed itself shows very small temperature variations, in the region of only 5° C. across its width and from top to bottom. It is therefore essentially isothermal. Most importantly, the degree of fluidisation judged by the variation in temperature within the system actually improves as the evolved vapour from the depolymerisation process takes over from the nitrogen flow as the principal fluidisation mechanism.

The invention will be further described in connection with the following examples, which are set forth for purposes of illustration only. Parts and percentages appearing in such examples are by weight unless otherwise stipulated.

EXAMPLE 1

Using approx. 90 kg of sand having a mean particle size of 120 μm, providing a non-fluidised bed height of 300 mm, PMMA was depolymerised at 390°–410° C. The products, as determined by gas chromatography, were 99.523% MMA, 0.144% methanol, 0.061% methyl propionate, 0.198% methyl isobutyrate, 0.036% butyl methacrylate and 0.038% styrene. Not only is the yield of MMA exceptionally high, but methyl isobutyrate is present at a very low level, i.e. below 0.25%. That level can itself be reduced by vacuum distillation.

EXAMPLE 2

Calculations based upon the theory of conventional fluidised beds show that the maximum depolymerisation rate for the experimental bed would be approximately 30 kg/h, provided that the necessary heat could be transferred to the particles of polymer. This limit is set by the superficial velocity at which bed material would be carried away and does not depend upon any temperature depolymerisation rate characteristics.

In an experiment parallel to Example 1, an average depolymerisation rate of 32.3 kg/h was observed for periods exceeding one hour, with peak activities estimated to be equivalent to 35–40 kg/h at a mean bed temperature of 410° C. The resulting monomer had a purity (by GLC) of 99.25–99.48%.

Calculations suggest that vapour-driven fluidisation becomes significant when a critical minimum polymer burden (equivalent to vapour sources spaced at 20–30 mm separations within bed) is exceeded in the bed; after which both the fluidisation process and most importantly the heat transfer coefficient achieved between the particles of the bed cease to be conventional functions of superficial gas flow as predicted by standard theories.

In a further test sequence, the temperature of the bed was allowed to decrease from an initial value of 350°–315° C. while the PMMA input was maintained at 16–20 kg/h.

On the basis of this and similar trials, it appears that the throughput is essentially independent of bed temperature at least in the range 460°–315° C. provided that the HTC is maintained at a value sufficient to achieve ablation of the particles of polymer.

EXAMPLE 3

The procedure of Example 1 was repeated, but replacing the silica by alumina having a particle diameter of 80–180 μm, mean diameter 110 μm. The temperature was 370° C. The MMA purity was approx. 99.7%; the methyl isobutyrate level was below 0.2%.

While the invention has been described in connection with certain preferred embodiments, it is not intended to limit the scope of the invention to the particular forms set forth, but, on the contrary, it is intended to cover such alternatives, modifications, and equivalents as may be included within the spirit and scope of the invention as defined by the appended claims.

What we claim is:

1. A depolymerisation process, comprising: heating a polymer in a fluidised bed, said bed comprising particles of an inert material at least 50 micrometers in diameter, at a temperature below the autoignition point of the corresponding monomer, such that the heat transfer coefficient is maintained at a value sufficient to ablate the polymer particles.

2. The process according to claim 1, wherein the monomer is methyl methacrylate.

3. The process according to claim 1, wherein the temperature is 300°–420° C.

4. The process according to claim 1, wherein the bed comprises particles of an inert material having a diameter of from 10 to 1000 μm.

5. The process according to claim 4, wherein the inert material is alumina.

6. The process according to claim 1, wherein the initial fluidisation medium comprises a controllable supply of inert gas.

7. The process according to claim 6, wherein the bed has an upper part and a lower part and the inert gas is circulated from the upper part of the bed to the lower part, via a condenser where entrained monomer is separated.

8. The process according to claim 1, further comprising means for continuously and controllably recycling bed material.

9. The process according to claim 1, wherein the fluidised bed is in a reaction chamber whose cross-section increases upwardly.

* * * * *